United States Patent
Park et al.

(10) Patent No.: US 9,968,333 B2
(45) Date of Patent: May 15, 2018

(54) METHOD AND APPARATUS FOR ANALYZING ELASTOGRAPHY OF TISSUE USING ULTRASOUND WAVES

(71) Applicant: Samsung Electronics Co., Ltd., Suwon-si (KR)

(72) Inventors: Ji-young Park, Yongin-si (KR); Ki-wan Choi, Anyang-si (KR); Hyoung-ki Lee, Seongnam-si (KR); Jong-hwa Won, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 212 days.

(21) Appl. No.: 13/919,303

(22) Filed: Jun. 17, 2013

(65) Prior Publication Data

US 2014/0046183 A1 Feb. 13, 2014

(30) Foreign Application Priority Data

Aug. 8, 2012 (KR) .................. 10-2012-0086937

(51) Int. Cl.
 *A61B 8/08* (2006.01)
 *A61B 8/00* (2006.01)

(52) U.S. Cl.
 CPC .............. *A61B 8/485* (2013.01); *A61B 8/085* (2013.01); *A61B 8/469* (2013.01); *A61B 8/483* (2013.01)

(58) Field of Classification Search
 CPC ......... A61B 8/085; A61B 8/469; A61B 8/483; A61B 8/485
 See application file for complete search history.

(56) References Cited

U.S. PATENT DOCUMENTS

| | | | |
|---|---|---|---|
| 5,810,731 A | 9/1998 | Sarvazyan et al. | |
| 6,374,674 B1 * | 4/2002 | Mine | A61B 8/14 600/443 |
| 6,520,913 B1 | 2/2003 | Pesavento et al. | |
| 7,252,004 B2 | 8/2007 | Fink et al. | |
| 9,043,156 B2 * | 5/2015 | Gallippi | A61B 8/485 702/19 |
| 2002/0010398 A1 | 1/2002 | Bonnefous | |

(Continued)

FOREIGN PATENT DOCUMENTS

| | | |
|---|---|---|
| JP | 2010-124852 | 6/2010 |
| JP | 2011-172730 | 9/2011 |

(Continued)

OTHER PUBLICATIONS

J. Ophir et al., "Elastography: A Quantitative Method for Imaging the Elasticity of Biological Tissues," *Ultrason Imaging* 13, pp. 111-134 (1991).

(Continued)

*Primary Examiner* — Michael Rozanski
(74) *Attorney, Agent, or Firm* — Staas & Halsey

(57) ABSTRACT

A method and apparatus for analyzing elastography of tissue using ultrasound waves, wherein elastography information of tissue in a region of interest (ROI) is analyzed by irradiating ultrasound waves for diagnosis towards the ROI to which a shear wave is induced from an ultrasound probe, receiving echo ultrasound waves, and acquiring three-dimensional (3D) ultrasound images with respect to the ROI.

14 Claims, 6 Drawing Sheets
(2 of 6 Drawing Sheet(s) Filed in Color)

(56) References Cited

U.S. PATENT DOCUMENTS

| | | | |
|---|---|---|---|
| 2004/0225215 A1 | 11/2004 | Querleux et al. | |
| 2005/0252295 A1 | 11/2005 | Fink et al. | |
| 2006/0264736 A1 | 11/2006 | Ehman et al. | |
| 2009/0124901 A1 | 5/2009 | Fink et al. | |
| 2010/0130865 A1 | 5/2010 | Sandrin et al. | |
| 2010/0240994 A1 | 9/2010 | Zheng | |
| 2012/0123263 A1 | 5/2012 | Osaka et al. | |
| 2012/0302883 A1* | 11/2012 | Kong et al. | 600/439 |
| 2014/0081135 A1* | 3/2014 | Choi et al. | 600/438 |

FOREIGN PATENT DOCUMENTS

| | | |
|---|---|---|
| JP | 2012-66027 | 4/2012 |
| KR | 10-2011-0129828 | 12/2011 |
| KR | 10-2012-0039545 | 4/2012 |

OTHER PUBLICATIONS

U.S. Appl. No. 13/868,460, filed Apr. 23, 2013, Ki-wan Choi, Samsung Electronics Co., Ltd.

* cited by examiner

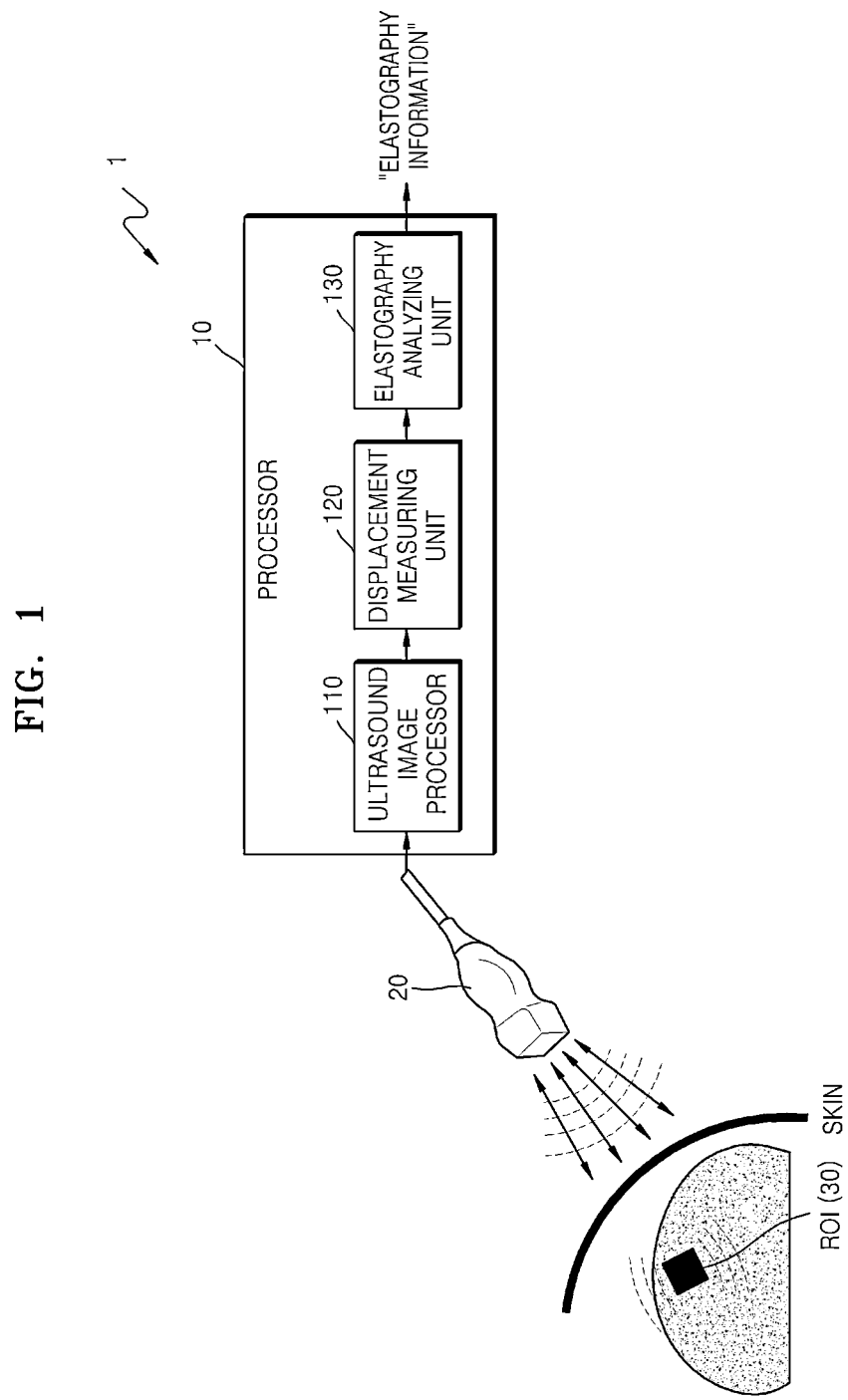

3D VOLUME ACQUISITION

3D PLANE SCAN

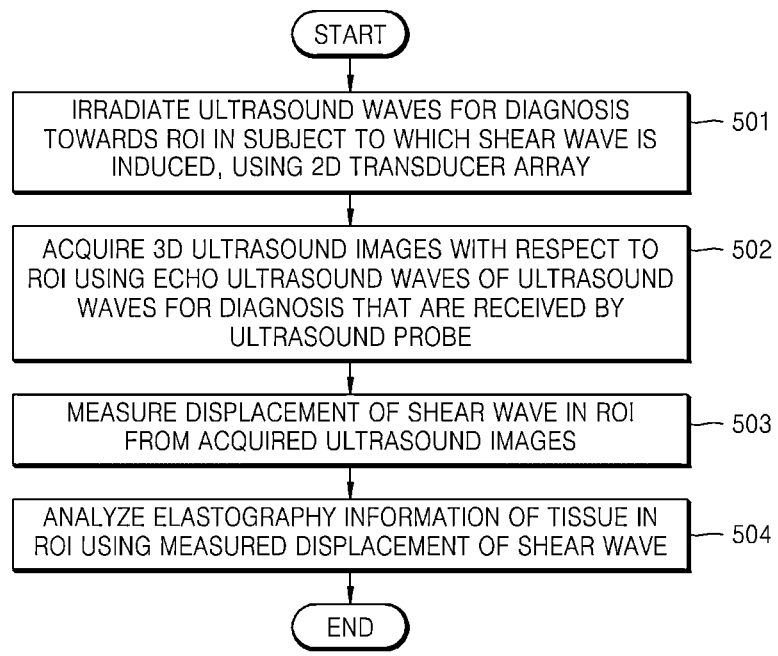

METHOD AND APPARATUS FOR ANALYZING ELASTOGRAPHY OF TISSUE USING ULTRASOUND WAVES

CROSS-REFERENCE TO RELATED APPLICATIONS

This application claims the benefit of Korean Patent Application No. 10-2012-0086937, filed on Aug. 8, 2012, in the Korean Intellectual Property Office, the disclosure of which is incorporated herein in its entirety by reference.

BACKGROUND

1. Field

One or more embodiments of the present disclosure relate to methods and apparatuses for analyzing elastography of tissue of a human or animal subject using ultrasound waves.

2. Description of the Related Art

To diagnose a disease, establish a treatment plan, or evaluate a treatment progress using ultrasound images in medical institutions, a medical practitioner reads ultrasound images of a patient, which are displayed on a monitor, to observe states or sequential histological changes of tumorous or cancerous tissue. However, since ultrasound images are read by a medical practitioner with the naked eye, the same ultrasound image may be analyzed differently depending on the angle of view of the medical practitioner, thereby making the potential for a measurement error large. In addition, occasionally, a medical practitioner incorrectly recognizes abnormal tissue, such as tumorous or cancerous tissue in ultrasound images as normal tissue, that is tissue without tumors or cancer.

However, recently, Computer-Aided Diagnosis (CAD) systems primarily discerning medical images, such as ultrasound images, Magnetic Resonance Imaging (MRI) images, and Computed Tomography (CT) images, and indicating the presence or absence of abnormal tissue, a location of the abnormal tissue, and the like to a medical practitioner have been developed. The CAD systems, which detect abnormal tissue by processing the presence or absence of abnormal tissue in a medical image, a size of the abnormal tissue, a location of the abnormal tissue, and the like using a computer system and provide a detection result to a medical practitioner to aid image diagnosis by the medical practitioner, may be used in combination with medical devices, such as an ultrasound device, an MRI device, and a CT device.

SUMMARY

Provided are methods and apparatuses for analyzing elastography of tissue in a subject using ultrasound waves.

Provided are computer-readable recording media storing a computer-readable program for executing the methods.

Additional aspects will be set forth in part in the description which follows and, in part, will be apparent from the description, or may be learned by practice of the presented embodiments.

According to an aspect of the present disclosure, a method of analyzing elastography of tissue using ultrasound waves includes: irradiating ultrasound waves for diagnosis towards a region of interest (ROI) in a subject, to which a shear wave is induced, from an ultrasound probe having a two-dimensional (2D) transducer array; acquiring three-dimensional (3D) ultrasound images with respect to the ROI using echo ultrasound waves of the ultrasound waves for diagnosis, which have been received by the ultrasound probe; measuring a displacement of the shear wave in the ROI from the acquired 3D ultrasound images; and analyzing information about elastography of tissue in the ROI using the measured displacement of the shear wave.

According to another aspect of the present disclosure, a computer-readable recording medium storing a computer-readable program for executing the method of analyzing elastography of tissue using ultrasound waves in a computer system is provided.

According to another aspect of the present disclosure, an apparatus for analyzing elastography of tissue using ultrasound waves includes: an ultrasound probe for irradiating ultrasound waves for diagnosis towards a region of interest (ROI) in a subject, to which a shear wave is induced, using a two-dimensional (2D) transducer array; an ultrasound image processor for acquiring three-dimensional (3D) ultrasound images with respect to the ROI using echo ultrasound waves of the ultrasound waves for diagnosis, which have been received by the ultrasound probe; a displacement measuring unit for measuring a displacement of the shear wave in the ROI from the acquired 3D ultrasound images; and an elastography analyzing unit for analyzing information about elastography of tissue in the ROI using the measured displacement of the shear wave.

According to another aspect of the present disclosure, a system to analyze elastography of tissue using ultrasound waves is provided. The system includes an ultrasound probe to irradiate a region of interest (ROI) in a subject with ultrasound waves thereby inducing a shear wave in the ROI and a processor. The processor includes an ultrasound image processor to acquire three-dimensional (3D) ultrasound images of the ROI using echo ultrasound waves provided by the ultrasound probe, wherein the echo ultrasound waves are obtained from the ultrasound waves after the ultrasound waves are reflected from the ROI or regions around the ROI, a displacement measuring unit to measure a displacement of the shear wave in the ROI based on the acquired 3D ultrasound images, and an elastography analyzing unit to analyze information about elastography of tissue in the ROI using the measured displacement of the shear wave.

BRIEF DESCRIPTION OF THE DRAWINGS

The patent or application file contains at least one drawing executed in color. Copies of this patent or patent application publication with color drawing(s) will be provided by the Office upon request and payment of the necessary fee. These and/or other aspects will become apparent and more readily appreciated from the following description of the embodiments, taken in conjunction with the accompanying drawings in which:

FIG. 1 is a block diagram of an apparatus for analyzing elastography of tissue using ultrasound waves, according to an embodiment of the present disclosure;

FIG. 5 is a flowchart illustrating a method of analyzing elastography of tissue using ultrasound waves, according to an embodiment of the present disclosure.

DETAILED DESCRIPTION

Figure 2A:
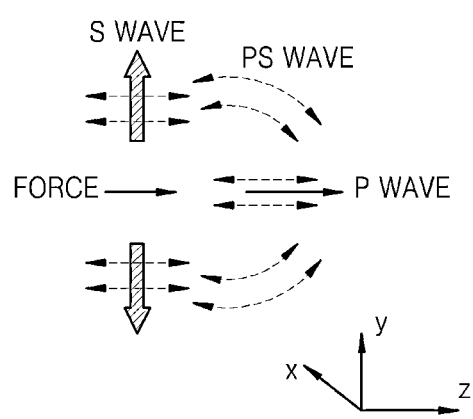
FIG. 2A is a diagram for describing a shear wave according to an embodiment of the present disclosure.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description.

FIG. 1 is a block diagram of an apparatus 1 for analyzing elastography of tissue using ultrasound waves, according to an embodiment of the present disclosure. Referring to FIG. 1, the apparatus 1 may include, for example, a processor 10 and an ultrasound probe 20. The processor 10 may include, for example, an ultrasound image processor 110, a displacement measuring unit 120, and an elastography analyzing unit 130.

Only hardware components associated with the current embodiment are described in FIG. 1 to prevent features of the current embodiment from being obscured. However, it will be understood by one of ordinary skill in the art that the apparatus 1 may further include other general-use hardware components.

Recently, systems, such as Computer-Aided Diagnosis (CAD) systems, primarily discerning medical images, such as ultrasound images, Magnetic Resonance Imaging (MRI) images, and Computed Tomography (CT) images, and providing the presence or absence of abnormal tissue, a location of the abnormal tissue, and the like to a medical practitioner have been used. The systems may detect abnormal tissue by processing the presence or absence of abnormal tissue in a medical image, a size of the abnormal tissue, a location of the abnormal tissue, and the like using a computer system and provide a detection result to a medical practitioner to aid image diagnosis by the medical practitioner.

The apparatus 1 may be used in systems such as the CAD systems described above. Ultrasound elastography technology may be used to diagnose tissue by analyzing elastography of the tissue and discerning a stiffness difference between normal tissue and abnormal tissue. In particular, the apparatus 1 may be used to discern a state of tissue in the human body, or in animal tissue, such as whether abnormal tissue, such as cancer, exists or whether tissue has been completely treated when the tissue is treated using High Intensity Focused Ultrasound (HIFU) or the like, by analyzing elastography of the tissue using ultrasound waves.

In general, it is known that abnormal tissue has a difference in stiffness compared with normal tissue, and the abnormal tissue may be discerned by analyzing this difference. Thus, abnormal tissue, such as cancerous tissue or tissue having a tumor, may have a higher elastography score than surrounding normal tissue. Thus, a shear modulus of the abnormal tissue is higher than that of the surrounding normal tissue. In addition, when tissue is treated by necrosing it using ultrasound waves for treatment, such as in HIFU, an elastography score of the tissue increases as necrosis of the tissue progresses. That is, a state change of tissue may be determined or monitored by an elastography of the tissue. Thus, if elastography of the tissue is perceived using ultrasound waves, a medical practitioner may noninvasively monitor a state of the tissue without having to view the tissue in the human body with the naked eye.

The apparatus 1 may be configured as a system capable of aiding image diagnosis by a medical practitioner in a medical institution and may be used to diagnose a disease, establish a treatment plan, and evaluate a treatment progress by providing a result of analyzing elastography of tissue using ultrasound waves. Alternatively, the apparatus 1 may be used to detect diseased tissue in a living animal or may be used to inspect animal tissue of a living or dead animal, such as to determine the quality of animal meat for human consumption. A configuration and operation of the apparatus 1 will now be described in more detail.

The ultrasound probe 20 induces a shear wave by radiating ultrasound waves upon a region of interest (ROI) 30 in the human body before elastography is analyzed. To quantitatively analyze the elastography using the ultrasound waves for diagnosis, Acoustic Radiation Force Impulses (AFRIs) equivalent to the ultrasound waves for diagnosis need to be applied to the human or animal body in advance to cause a displacement of tissue. That is, the AFRIs induce a shear wave to the tissue to cause the displacement of the tissue.

FIG. 2A is a diagram for describing a shear wave according to an embodiment of the present disclosure. Referring to FIG. 2A, when a force of a point impulse is applied along a z-axis direction, a P wave that is a longitudinal wave, an S wave that is a transverse wave, and a PS wave that is a coupling wave of the P wave and the S wave are generated. The shear wave is a wave vibrating along a wave traveling direction and traveling along a y-axis direction from a vibration source to which the force is applied, i.e., the S wave.

It is described in the current embodiment for convenience of description that the ultrasound waves for diagnosis from the ultrasound probe 20 are used for the force of the point impulse for inducing the shear wave. However, the current embodiment is not limited thereto, and a treatment ultrasound device, such as an HIFU device, or an oscillator located outside the apparatus 1 may also be used to induce the shear wave. That is, it will be understood by one of ordinary skill in the art that a device for inducing the shear wave to the ROI 30 is not limited to any one device and may include a variety of different devices.

Figure 2B:
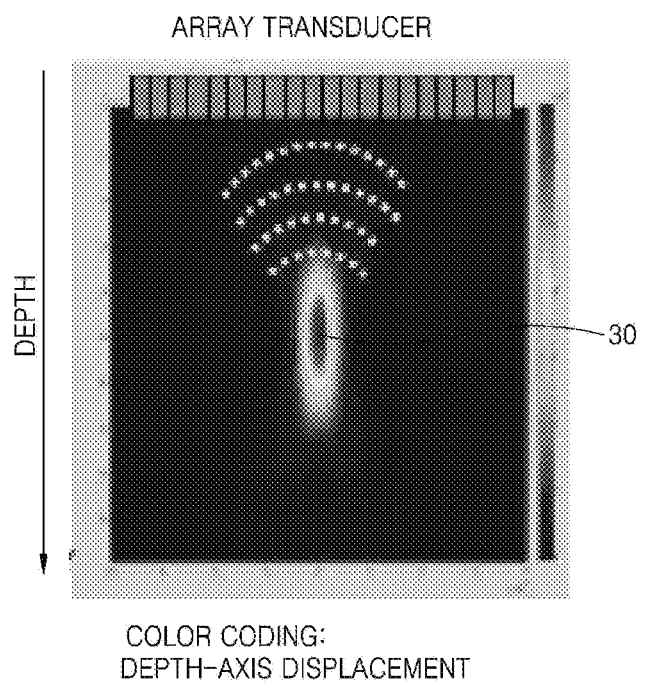
FIG. 2B is an image showing that a shear wave is induced to a region of interest (ROI) according to an embodiment of the present disclosure.

FIG. 2B is an image showing a shear wave being induced in the ROI 30 according to an embodiment of the present disclosure. Referring to FIG. 2B, the ultrasound probe 20 induces the shear wave in the ROI 30 by radiating the ultrasound waves for diagnosis along a depth-axis direction to form a focal point on the ROI 30 under the skin of the human body, thereby irradiating the ROI.

Referring back to FIG. 1, the ultrasound probe 20 radiate the ultrasound waves towards the ROI 30 thereby irradiating the ROI 30 to obtain ultrasound images of the ROI 30 and regions around the ROI 30 after the shear wave is induced in the ROI 30.

The ultrasound probe 20 may radiate plane waves by beamforming the ultrasound waves in a defocusing method. The plane waves are used in the defocusing method is to allow the shear wave to be observed in a wider range.

In more detail, the ultrasound probe 20 may use the defocusing method so that a displacement of the shear wave is observed in a wider range than would be observed if a focusing method were used. In addition, by using plane waves having a strength that is maintained relatively constant even when the plane waves reach a location deep in the human body, a displacement of the shear wave may be more correctly observed than spherical waves having a strength that weakens as they reach a deep location.

The ultrasound probe 20 may include a 2D transducer array to acquire 3D ultrasound images at high speed, as described with reference to FIGS. 3A and 3B.

Figure 3A:
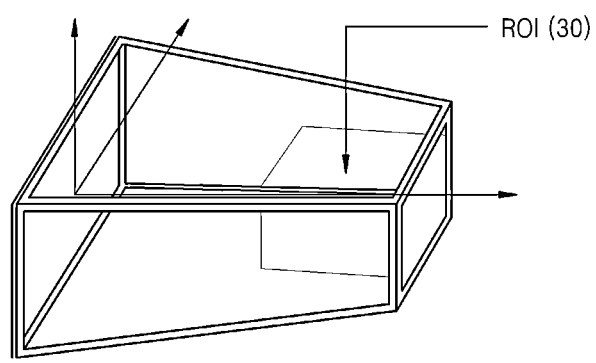
FIG. 3A is a perspective view showing a case where ultrasound waves for diagnosis are irradiated by a 3D volume acquisition method according to an embodiment of the present disclosure.

FIG. 3A is a perspective view showing ultrasound waves being radiated using a 3D volume acquisition method according to an embodiment of the present disclosure. Referring to FIG. 3A, the ultrasound probe 20 may irradiate the ROI 30 with the ultrasound waves using the 2D transducer array to scan a 3D volume of the ROI 30 and regions around the ROI 30 at once, that is, to scan the 3D volume simultaneously or within a very short period of time.

Figure 3B:
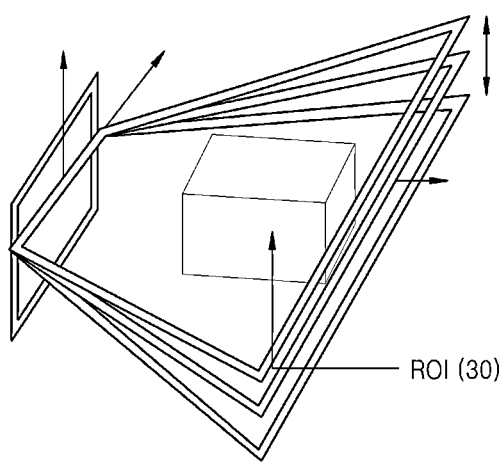
FIG. 3B is a perspective view showing a case where ultrasound waves for diagnosis are irradiated by a 3D plane scan method according to an embodiment of the present disclosure.

FIG. 3B is a perspective view showing a case where the ultrasound waves are radiated using a 3D plane scan method according to an embodiment of the present disclosure. Referring to FIG. 3B, the ultrasound probe 20 may irradiate the ROI 30 with the ultrasound waves using the 2D transducer array to scan the ROI 30 and regions around the ROI 30 on a plane basis and generate 3D volume data with respect to the ROI 30.

Referring back to FIG. 1, the ultrasound probe 20 receives echo ultrasound waves. The echo ultrasound waves are the original ultrasound waves after being reflected from the ROI 30 and the regions around the ROI 30. As described above, since the ultrasound probe 20 radiates the ultrasound waves using either of the 2D transducer array in the 3D volume acquisition method or the 3D plane scan method, the ultrasound probe 20 may receive echo ultrasound waves including 3D information about the ROI 30 and the regions around the ROI 30.

In general, it is known that a wave speed of the shear wave is about 1 m/s to about 10 m/s. Thus, to observe the shear wave with a resolution of several mm, ultrasound images may need to be acquired in units of thousands of frames per second. To acquire ultrasound images of thousands of frames per second, the ultrasound waves for diagnosis need to be irradiated and received at a speed faster than the wave speed of the shear wave. In this case, since an existing 3D line scan method can scan only a single scan line at a time, ultrasound images of thousands of frames per second cannot be acquired and it may be difficult to correctly measure the movement of the shear wave using the 3D line scan method. Thus, by instead using the methods shown in FIG. 3A or 3B, 3D, ultrasound images of thousands of frames per second may be acquired using the 2D transducer array, thereby correctly measuring the movement of the shear wave.

The ultrasound image processor 110 may acquire 3D ultrasound images of thousands of frames per second by processing the echo ultrasound waves received by the ultrasound probe 20. In other words, the ultrasound image processor 110 may acquire 3D ultrasound images of thousands of frames per second by beamforming the echo ultrasound waves received by the ultrasound probe 20. Since a typical process of processing ultrasound images by using echo ultrasound waves would be apparent to one of ordinary skill in the art, a detailed description thereof is omitted.

The displacement measuring unit 120 measures a displacement of the shear wave in the ROI 30 from the acquired 3D ultrasound images. Since the 3D ultrasound images are acquired by the ultrasound image processor 110 as described above, the displacement of the shear wave that is measured by the displacement measuring unit 120 corresponds to measured 3D movement of the shear wave. That is, the measured displacement of the shear wave has displacement components corresponding to the x-, y-, and z-axes in an arbitrary 3D coordinate space.

Since a typical process of measuring a displacement of a shear wave by analyzing movement of the shear wave, which is shown in ultrasound images of thousands of frames per second, would be apparent to one of ordinary skill in the art, a detailed description thereof has been omitted.

The elastography analyzing unit 130 analyzes elastography information of tissue in the ROI 30 using the measured displacement of the shear wave. The elastography information analyzed in the current embodiment may include a shear modulus.

The elastography analyzing unit 130 may calculate a shear modulus of the tissue in the ROI 30 using the displacement components corresponding to 3D coordinate axes (x-, y-, and z-axes) that are included in the measured displacement of the shear wave. In this case, the elastography analyzing unit 130 may calculate the shear modulus using a wave equation with respect to the shear wave.

In more detail, the elastography analyzing unit 130 may calculate a moving speed of the shear wave using the displacement components corresponding to the 3D coordinate axes that are included in the measured displacement of the shear wave.

$$\frac{\partial^2 u}{\partial t^2} = C_S^2 \cdot \left( \frac{\partial^2 u}{\partial x^2} + \frac{\partial^2 u}{\partial y^2} + \frac{\partial^2 u}{\partial z^2} \right) \quad (1)$$

In Equation 1, u denotes a displacement of a shear wave and $C_s$ denotes a moving speed of the shear wave. Although the elastography analyzing unit 130 may calculate the moving speed $C_s$ of the shear wave using Equation 1 in the current embodiment, the current embodiment is not limited thereto.

The elastography analyzing unit 130 may calculate a shear modulus of the tissue in the ROI 30 using the calculated moving speed $C_s$ of the shear wave.

$$G = \rho \times C_S^2 \quad (2)$$

In Equation 2, G denotes a shear modulus, and p denotes density of a medium. Since the elastography analyzing unit 130 may calculate the moving speed $C_S$ of the shear wave using Equation 1 as described above and p is an already known value, the elastography analyzing unit 130 may calculate the shear modulus G using Equation 2. Although the elastography analyzing unit 130 calculates the shear modulus G using Equation 2 in the current embodiment, the current embodiment is not limited thereto.

If the elastography analyzing unit 130 analyzes the shear modulus G in units of at least two frames in the 3D ultrasound images, the elastography analyzing unit 130 may calculate a final shear modulus G by calculating a mean value of the calculated shear moduli G.

Alternatively, the elastography analyzing unit 130 may calculate the shear modulus G using Equation 3 below.

$$\rho \frac{\partial^2 u}{\partial t^2} = G(x, y, z) \left( \frac{\partial^2 u_z}{\partial x^2} + \frac{\partial^2 u_z}{\partial y^2} + \frac{\partial^2 u_z}{\partial z^2} \right) \Leftrightarrow G(x, y, z) = \rho \frac{\frac{\partial^2 u}{\partial t^2}}{\frac{\partial^2 u_z}{\partial x^2} + \frac{\partial^2 u_z}{\partial y^2} + \frac{\partial^2 u_z}{\partial z^2}} \quad (3)$$

That is, the elastography analyzing unit 130 may calculate the shear modulus G using Equation 3 in which Equations 1 and 2 have been combined.

As described above, since the ultrasound image processor 110 acquires the 3D ultrasound images at thousands of frames per second, and the displacement measuring unit 120 measures the displacement of the shear wave having the 3D displacement components, the elastography analyzing unit 130 may calculate the shear modulus G by considering all of the 3D displacement components. That is, the shear modulus G calculated by the elastography analyzing unit 130 has a more accurate value than when it is calculated by two-dimensionally measuring the displacement.

Thus, a shear modulus may be more correctly analyzed when the shear modulus is analyzed based on 3D ultrasound images acquired by the ultrasound probe 20 having a 2D transducer array according to the current embodiment than when the shear modulus is analyzed based on 2D ultrasound images acquired by an ultrasound probe having a 1D transducer array.

Figure 4A:
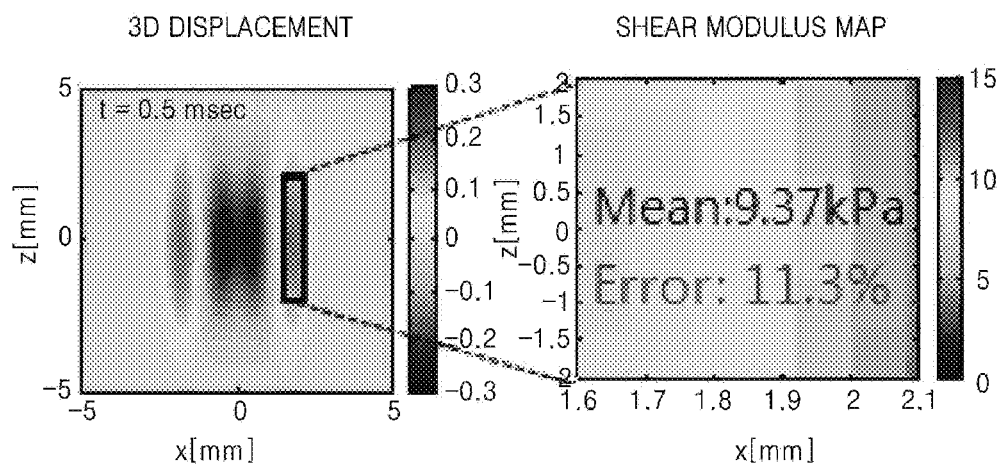
FIG. 4A is an image showing a simulation result of a case where a shear modulus is analyzed from 2D ultrasound images acquired using an existing ultrasound probe having a 1D transducer array.

FIG. 4A is an image showing a simulation result of a case where a shear modulus is analyzed from 2D ultrasound images acquired using an existing ultrasound probe having a 1D transducer array. Referring to FIG. 4A, a displacement map showing a 2D displacement of a shear wave and a corresponding shear modulus map are shown.

Figure 4B:
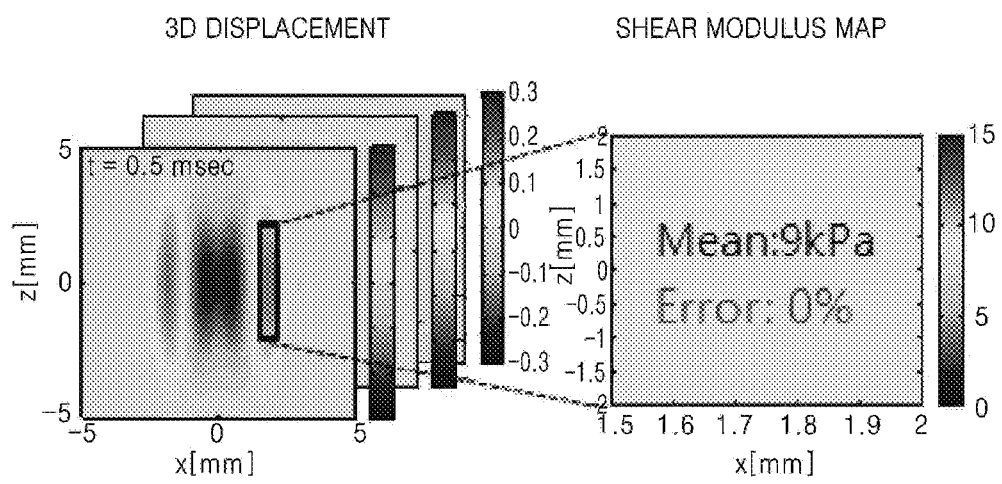
FIG. 4B is an image showing a simulation result of a case where a shear modulus is analyzed from 3D ultrasound images acquired using an ultrasound probe having a 2D transducer array according to an embodiment of the present disclosure.

FIG. 4B is an image showing a simulation result of a case where a shear modulus is analyzed from 3D ultrasound images acquired using an ultrasound probe having a 2D transducer array according to an embodiment of the present disclosure. Referring to FIG. 4B, a displacement map showing a 3D displacement of a shear wave and a corresponding shear modulus map are shown.

Comparing them with each other, when 2D ultrasound images are acquired using the ultrasound probe having a 1D transducer array according to FIG. 4A, since a displacement of the shear wave may not be considered along all directions in a 3D space, the shear modulus may not be correctly analyzed.

However, when 3D ultrasound images are acquired using the ultrasound probe having a 2D transducer array according to the current embodiment, since a displacement of the shear wave may be considered along all directions (x-, y-, and z-axes) in a 3D space, the shear modulus may be more correctly analyzed than in the case of FIG. 4A.

Referring back to FIG. 1, the elastography analyzing unit 130 provides elastography information based on the calculated shear modulus. Although not shown in FIG. 1, the elastography information, such as the shear modulus analyzed by the elastography analyzing unit 130, may be provided to a user, such as a medical practitioner, through a display device (not shown) and may be used to perceive a state or a characteristic change in tissue.

FIG. 5 is a flowchart illustrating a method of analyzing elastography of tissue using ultrasound waves, according to an embodiment of the present disclosure. Referring to FIG. 5, the method includes operations sequentially processed by the apparatus 1 shown in FIG. 1, although the operations may alternatively be performed by apparatuses or systems other than apparatus 1. Thus, although omitted below, the descriptions of the apparatus 1 above also apply to the method according to the current embodiment.

In operation 501, the ultrasound probe 20 may irradiate ROI 30 with ultrasound waves using a 2D transducer array, thereby inducing a shear wave in ROI 30.

In operation 502, the ultrasound image processor 110 may acquire 3D ultrasound images with respect to the ROI 30 using echo ultrasound waves, which are echos of the ultrasound waves that are received by the ultrasound probe 20.

In operation 503, the displacement measuring unit 120 may measure a displacement of the shear wave in the ROI 30 from the acquired ultrasound images.

In operation 504, the elastography analyzing unit 130 may analyze elastography information of tissue in the ROI 30 using the measured displacement of the shear wave.

As described above, according to the one or more of the above embodiments of the present disclosure, since three-dimensional ultrasound images with respect to an ROI are obtained at a relatively high speed, a displacement of a shear wave induced in tissue in the human body may be correctly measured. In addition, since the displacement of the shear wave is three-dimensionally measured using the three-dimensional ultrasound images, a shear modulus of the tissue in the human body may be accurately calculated and provided. Further, decision-making by a medical practitioner in diagnosis or treatment of a disease of a patient may be aided using analyzed information about elastography.

The embodiments of the present disclosure can be written as computer programs and can be implemented in general-use digital computers that execute the programs using a computer-readable recording medium. In addition, a structure of data used in the embodiments of the present disclosure may be recorded on a computer-readable recording medium using various means. Examples of the computer-readable recording medium include storage media, such as magnetic storage media (e.g., ROM, floppy disks, hard disks, etc.) and optical recording media (e.g., CD-ROMs, or DVDs).

In addition, other embodiments of the present disclosure can also be implemented through computer-readable code/instructions in/on a medium, e.g., a computer-readable recording medium, to control at least one processing element to implement any above described embodiment. The computer-readable recording medium can correspond to any medium/media permitting the storage and/or transmission of the computer-readable code.

The computer-readable code can be recorded/transferred on a medium in a variety of ways, with examples of the computer-readable recording medium including recording media, such as magnetic storage media (e.g., ROM, floppy disks, hard disks, etc.) and optical recording media (e.g., CD-ROMs, or DVDs), and transmission media such as Internet transmission media. Thus, the medium may be such a defined and measurable structure including or carrying a signal or information, such as a device carrying a bitstream according to one or more embodiments of the present disclosure. The media may also be a distributed network, so that the computer-readable code is stored/transferred and executed in a distributed fashion. Furthermore, the process-

What is claimed is:

1. A method of analyzing elastography of tissue using ultrasound waves, the method comprising:
   inducing a shear wave on the tissue in a human body by Acoustic Radiation Force Impulse (ARFI) using an ultrasound probe having a two-dimensional (2D) transducer array;
   irradiating ultrasound waves using the ultrasound probe to acquire three-dimensional (3D) ultrasound data with respect to the tissue;
   acquiring the 3D ultrasound data using echo ultrasound waves of the ultrasound waves and a 3D volume acquisition method in which a 3D volume of the tissue is scanned by the 2D transducer array;
   calculating 3D displacement components of the shear wave in the tissue based on the acquired 3D ultrasound data;
   calculating a speed of the shear wave using the calculated 3D displacement components;
   calculating a shear modulus of the tissue using the speed of the shear wave;
   calculating a final shear modulus by calculating a mean value of the shear modulus in units of at least two frames in 3D ultrasound images; and
   displaying a 3D displacement map of the shear wave and a shear modulus map based on the final shear modulus.

2. The method of claim 1, wherein the calculating the 3D displacement components of the shear wave in the tissue comprises calculating 3D displacement components of a shear modulus of the tissue using a wave equation with respect to the shear wave.

3. The method of claim 1, wherein the acquiring of the 3D ultrasound data comprises selectively acquiring the 3D ultrasound data using the 3D volume acquisition method and using a 3D plane scan method in which 3D volume data of the tissue is generated by scanning the tissue in a plane unit.

4. The method of claim 1, wherein the irradiating with the ultrasound waves is performed for diagnosis of the human body and comprises irradiating the ultrasound waves of plane waves by beamforming the ultrasound waves in a defocusing method.

5. The method of claim 1, wherein the acquiring of the 3D ultrasound data comprises acquiring the 3D ultrasound data by beamforming the echo ultrasound waves with respect to the tissue.

6. The method of claim 1, further comprising displaying at least one image representing the 3D displacement components of the shear wave.

7. The method of claim 1, further comprising displaying at least one 3D image using the calculated speed of the shear wave.

8. The method of claim 1, further comprising displaying a modulus of elasticity based on the calculated speed of the shear wave.

9. The method of claim 1, wherein the speed of the shear wave is calculated using the following equation:

$$\frac{\partial^2 u}{\partial t^2} = C_s^2 \left( \frac{\partial^2 u}{\partial x^2} + \frac{\partial^2 u}{\partial y^2} + \frac{\partial^2 u}{\partial z^2} \right)$$

where u denotes a displacement of the shear wave, t denotes time, and x, y, and z denote the respective calculated 3D displacement components.

10. The method of claim 9, wherein the shear modulus of the tissue is calculated using the following equation:

$$G = p \times C_s^2$$

where G denotes the shear modulus of the tissue, and p denotes a density of the tissue.

11. A non-transitory computer-readable recording medium storing a computer-readable program for executing a method comprising:
   inducing a shear wave on a tissue in a human body by Acoustic Radiation Force Impulse (ARFI) using an ultrasound probe having a two-dimensional (2D) transducer array;
   irradiating ultrasound waves using the ultrasound probe to acquire three-dimensional (3D) ultrasound data with respect to the tissue;
   acquiring the 3D ultrasound data using echo ultrasound waves of the ultrasound waves and a 3D volume acquisition method in which a 3D volume of the tissue is scanned by the 2D transducer array;
   calculating 3D displacement components of the shear wave in the tissue based on the acquired 3D ultrasound data;
   calculating a speed of the shear wave using the calculated 3D displacement components;
   calculating a shear modulus of the tissue using the speed of the shear wave;
   calculating a final shear modulus by calculating a mean value of the shear modulus in units of at least two frames in 3D ultrasound images; and
   displaying a 3D displacement map of the shear wave and a shear modulus map based on the final shear modulus.

12. An apparatus for analyzing elastography of tissue using ultrasound waves, the apparatus comprising:
   an ultrasound probe having a two-dimensional (2D) transducer array;
   a display;
   at least one hardware processor;
   computer readable memory comprising instructions that, when executed by the at least one hardware processor, perform operations comprising:
   controlling the ultrasound probe to induce a shear wave on the tissue in a human body by Acoustic Radiation Force Impulse (ARFI);
   controlling the ultrasound probe to irradiate ultrasound waves to acquire three-dimensional (3D) ultrasound data with respect to the tissue;
   acquiring the 3D ultrasound data using echo ultrasound waves of the ultrasound waves and a 3D volume acquisition method in which a 3D volume of the tissue is scanned by the 2D transducer array;

calculating 3D displacement components of the shear wave in the tissue based on the acquired 3D ultrasound data;

calculating a speed of the shear wave using the calculated 3D displacement components;

calculating a shear modulus of the tissue using the speed of the shear wave;

calculating a final shear modulus by calculating a mean value of the shear modulus in units of at least two frames in 3D ultrasound images; and displaying a 3D displacement map of the shear wave and a shear modulus map based on the final shear modulus.

13. The apparatus of claim 12, wherein the controlling the ultrasound probe to irradiate the ultrasound waves comprises irradiating the ultrasound waves of plane waves by beamforming the ultrasound waves in a defocusing method and wherein the irradiating of the ultrasound waves is performed for diagnosis of the human body.

14. The apparatus of claim 12, wherein the acquiring of the 3D ultrasound data comprises acquiring the 3D ultrasound data by beamforming the echo ultrasound waves with respect to the tissue.

* * * * *